United States Patent
Matson et al.

(10) Patent No.: US 6,911,219 B2
(45) Date of Patent: Jun. 28, 2005

(54) PARTIALLY ACETALIZED POLYVINYL ALCOHOL EMBOLIZATION PARTICLES, COMPOSITIONS CONTAINING THOSE PARTICLES AND METHODS OF MAKING AND USING THEM

(75) Inventors: Louis R. Matson, El Dorado Hills, CA (US); Donald K. Brandom, Davis, CA (US)

(73) Assignee: Surgica Corporation, El Dorado Hills, CA (US)

( * ) Notice: Subject to any disclaimer, the term of this patent is extended or adjusted under 35 U.S.C. 154(b) by 386 days.

(21) Appl. No.: 10/133,177

(22) Filed: Apr. 25, 2002

(65) Prior Publication Data

US 2003/0059371 A1 Mar. 27, 2003

Related U.S. Application Data

(60) Provisional application No. 60/324,920, filed on Sep. 27, 2001.

(51) Int. Cl.$^7$ .......................... A61K 9/50; A61K 51/02; A61M 36/14
(52) U.S. Cl. ....................... 424/501; 424/1.1; 424/1.29; 424/1.33; 424/1.81; 424/1.85
(58) Field of Search ........................ 424/501, 1.1, 1.29, 424/1.33, 1.81, 1.85

(56) References Cited

U.S. PATENT DOCUMENTS

| | | | |
|---|---|---|---|
| 5,895,411 A | | 4/1999 | Irie |
| 5,925,683 A | * | 7/1999 | Park .................... 514/772.1 |
| 6,160,025 A | | 12/2000 | Slaikeu et al. |
| 6,191,193 B1 | | 2/2001 | Lee et al. |

OTHER PUBLICATIONS

Barr, J.D. et al. (1998). "Polyvinyl Alcohol Foam Particle Sizes and Concentrations Injectable through Microcatheters," *JVIR* 9(1): 113–118.

Beese, R.C. et al. (2000). "Renal Angiography Using Carbon Dioxide," *British Journal of Radiology*, 73: 3–6.

Chawla, M.S. (1998). "*In Vivo* Magnetic Resonance Vascular Imaging Using Laser–Polarized $^3$He Microbubbles," *Proc. Nat. Acad. Sci, USA* 95: 10832–10835.

Chawla, M. "Hyperpolarized Gas as a Vascular Contrast Agent," *Center for In Vivo Microscopy* Located at <http://www.civm.mc.duke.edu/civmProjects/HPContrast/HPContrast.html> visited on Jul. 25, 2002. (2 pages total.).

Derdeyn, C.P. et al. (1995). "Polyvinyl Alcohol Particle Size and Suspension Characteristics," *American Journal of Neuroradiology* 16: 1335–1343.

Mandai, S. et al. (1992). "Direct Thrombosis of Aneurysms with Cellulose Acetate Polymer. Part I: Results of Thrombosis in Experimental Aneurysms," *J. Neurosurgery* 77: 497–500.

Novak, D. (1990). "Embolization Materials, "*In Interventional Radiology*. Dondelinger, R.F. et al, eds., Thieme Medical Publishers, NY, pp. 295–313.

Sugawara, T. et al. (1993). "Experimental Investigations Concerning a New Liquid Embolization Method: Combined Administration of Ethanol–Estrogen and Polyvinyl Acetate," *Neuro Med Chir (Tokyo)* 33: 71–76.

Taki, W. et al. (1990). "A New Liquid Material for Embolization of Arteriovenous Malformations,"*AJNR* 11: 163–168.

Vinters, H.V. et al. (1985). "The Hisotoxicity of Cyanoacrylates: A Selective Review," *Neuroradiology* 27: 279–291.

* cited by examiner

*Primary Examiner*—Carlos A. Azpuru
(74) *Attorney, Agent, or Firm*—Morrison & Foerster LLP

(57) ABSTRACT

This relates to partially acetalized polyvinyl alcohol embolization particles suitable for implanting in the human body, to compositions containing those particles, and to methods of making and using them.

112 Claims, No Drawings

PARTIALLY ACETALIZED POLYVINYL ALCOHOL EMBOLIZATION PARTICLES, COMPOSITIONS CONTAINING THOSE PARTICLES AND METHODS OF MAKING AND USING THEM

RELATED APPLICATIONS

We claim priority to provisional Patent Application No. 60/324,920, filed Sep. 27, 2001, entitled "Tunable PVA Foam Embolization Particles" by Louis Russell Matson and Donald K. Brandom and incorporate that provisional application by reference.

FIELD OF THE INVENTION

This relates to partially acetalized polyvinyl alcohol embolization particles suitable for implanting in the human body, to compositions containing those particles (particularly when those compositions are generally homogeneous), and to methods of making and using them.

BACKGROUND OF THE INVENTION

This invention relates to partially acetalized polyvinyl alcohol embolization particles or compositions (also known as "sponge" or foam particles) and to injectable compositions that may be introduced into or injected into the body perhaps via a catheter to form occlusive masses in a selected body region. One variation of the material is a particle composition in which the particles have physical parameters that, when those particles are produced or selected to complement the liquid medium used to carry the particles into the body, do not plug or tend not to plug the devices used to introduce the materials into the body. The desirable homogeneity of the suspension or composition provides two key functions. First, it imparts a non-clogging property since the particles are not allowed to aggregate. A second, subtler result is the evenness of the delivery of the particles through the catheter. Since the particles do not collect into a bolus before delivery, the physician is able more accurately to control the time and quantity of delivery. Although this may seem to be a coupled property, it is not. For example, purely spherical smooth surface particles that are not homogeneously suspended could be delivered without clogging. However, they would be injected en masse without fine control. This is an important distinction.

One example of the particle-liquid medium composition entails a composition in which the particles are substantially suspended in the liquid medium for a period of time suitable for passage of the particle-liquid medium through the step of introducing the combination to a chosen site in the body without substantial plugging or agglomeration in the delivery apparatus.

In use, the compositions may be introduced into the human body to block blood flow to portions of malfunctioning human organs such as the kidney, spleen, and liver or to block blood flow into the malfunctioning regions of blood vessels such as arterio-venous malformations (AVM) and aneurysms. Certainly the compositions may be used to occlude vessels providing blood both to malignant and to benign tumors. This type of treatment is often employed for uterine fibroids, benign uterine smooth muscle tumors.

"Embolization" is the generic term for the artificial blocking of blood flow. Embolization of a vessel to an organ or in an organ may be used for a number of reasons. Vessel embolization may be used, for instance, for: 1) control of bleeding caused by trauma, 2) prevention of profuse blood loss during an operation requiring dissection of blood vessels, 3) obliteration of a portion of or of a whole organ having a tumor, or 4) blocking of blood flow into abnormal blood vessel structures such as AVM's and aneurysms.

There are a variety of materials and devices which have been used for embolization. These include platinum and stainless steel microcoils, and polyvinyl alcohol sponges (Ivalon). See, *Interventional Radiology*, Dandlinger et al, ed., Thieme, N.Y., 1990:295–313. Liquid embolic agents come in a variety of forms, e.g., cyanoacrylate glues (n-butyl and iso-butyl cyanoacrylate glue); solutions of partially hydrolyzed polyvinylacetate; cellulose diacetate polymers in biocompatible solvents such as dimethylsulfoxide, analogues and homologues of dimethylsulfoxide, and ethanol; and cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid in biocompatible solvents such as dimethylsulfoxide, ethanol and acetone.

Of these, the cyanoacrylate glues may have an advantage in ease of delivery in that they are liquid embolics. However, the constituent cyanoacrylate polymers have the disadvantage of being biodegradable. The degradation product, formaldehyde, is highly toxic to the neighboring tissues. See, Vinters et al, "The Histotoxocity of Cyanoacrylate: A Selective Review", *Neuroradiology* 1985; 27:279–291. Another disadvantage of cyanoacrylate materials is that the polymer may adhere both to the blood vessel and to the tip of the catheter. Thus, physicians must retract the catheter immediately after injection of the cyanoacrylate embolic material or risk adhesion of the cyanoacrylate and the catheter to the vessel.

The other liquid embolic materials listed just above are precipitative materials. See, Sugawara et al, "Experimental Investigations Concerning a New Liquid Embolization Method: Combined Administration of Ethanol-Estrogen and Polyvinyl Acetate", *Neuro Med Chir* (*Tokyo*) 1993; 33:71–76; Taki et al, "A New Liquid Material for Embolization of Arterio-Venous Malformations", *AJNR* 1990:11:163–168; Mandai et al, "Direct Thrombosis of Aneurysms with Cellulose Acetate Polymer. Part I: Results of Thrombosis in Experimental Aneurysms." *J Neurosurgery* 1992; 77:493–500. These materials employ a different mechanism in forming synthetic emboli than do the cyanoacrylate glues. Cyanoacrylate glues are monomeric and rapidly polymerize upon contact with blood. Precipitative materials, on the other hand, are pre-polymerized chains in which the polymer is dissolved in a solvent that is miscible with blood, but precipitate into an aggregate upon contact with that blood.

The first such precipitative material used in this way was polyvinyl acetate (PVAc). Takahashi et al. dissolved the polymer in an ethanol/water mixture and delivered the mixture to an AVM for embolization. Also, poly(ethylene-co-vinyl alcohol) ("EVAL") and cellulose acetate (CA) dissolved in 100% DMSO have also been used in clinical procedures. See, Taki et al, "A New Liquid Material for Embolization of Arterovenous Malformations", *AJNR* 1990; 11:163–168 and Mandai et al, "Direct Thrombosis of Aneurysms with Cellulose Polymer: Part I: Results of Thrombosis in Experimental Aneurysms", *J Neurosurgery* 1992; 77:493–500. Partially hydrolyzed polyvinyl acetate in ethanol is also used, particularly for treatment of hepatic tumors. See, U.S. Pat. No. 6,160,025 (Slaikeau et al) and U.S. Pat. No. 5,925,683 (Park et al).

One potential problem in use of the precipitating polymers mentioned above is due to the use of organic solvents to dissolve the polymers, i.e., ethanol for PVAc and DMSO for EVAL and CA. These materials are strong organic solvents that can dissolve the catheter hub, and, in the case of DMSO, can damage microcapillary vessels and surrounding tissues. These solvents are also known to cause vasospasm of blood vessels. Although PVAc is soluble in solvents which are milder than those needed for dissolution of EVAL or CA, a PVAc solution has a problem of its own: its radio-opacity is very low, i.e., the contrast concentration is only 100 mg I/ml equivalent.

Polyvinyl alcohol particles have been used to embolize various sites for a number of years. See, Barr et al, "Polyvinyl Alcohol Foam Particle Sizes and Concentrations Injectable through Microcatheters", JVIR 1998; 9:113–115 However, since these embolics are sponge-like and compressible, there is a potential for clogging in the catheters used for delivering the particles to the selected site in the body. See, Darden et al, "Polyvinyl Alcohol Particle Size and Suspension Characteristics", *American Journal of Neuroradiology* June 1995; 16:1335–1343. These particles have even been mounted on wires to achieve delivery without clumping. See, Irie, U.S. Pat. No. 5,895,411. Others have added dispersants to the particles. See, Lee et al, U.S. Pat. No. 6,191,193

None of the cited references suggest the tailoring of physical and chemical characteristics of PVA particles to complement the density of the liquid medium used to carry the particles into the body and thereby form a highly dispersed composition of partially acetalized PVA particles in that liquid medium. Those references do not show a composition in which the particles tend not to clump nor to aggregate in the delivery equipment during an embolization procedure.

SUMMARY OF THE INVENTION

This invention includes a composition for forming an occlusion in a body opening or cavity that is made up of a combination of hydrated, partially acetalized, polyvinyl alcohol foam particles having particle size, pore size, and particle porosity and selected injectable, biologically acceptable, liquid media. The liquid media has a liquid medium specific gravity, generally in a range having a lower limit of about 1.0 and has an upper limit of about 1.50, although the liquid medium specific gravity may fall in a range with a lower limit of about 1.1 and an upper limit of about 1.40, or a lower limit of about 1.15 and an upper limit of about 1.40.

The liquid medium may be made up of one or more members selected from the group consisting of saline solution, radio-opacifiers, antibiotics, chemotherapy drugs, pharmaceuticals, growth factors, anti-growth factors, and natural and synthetic hormones or, perhaps one or more imaging or contrast agents. The radio-opacifiers may comprise one or more iodine-based imaging or contrast agents such as the well known and commercially available Oxilan 300, Oxilan 350, Ultravist 150, Ultravist 240, Ultravist 300, Ultravist 370, and Omnipaque 350.

The composition may include gaseous negative contrast agents for flouroscopy such as $CO_2$ and gaseous contrast agents for Magnetic Resonance (MR) imaging techniques such as hyperpolarized gases (e.g., inert gases such as helium, xenon, and argon).

For certain uses, the liquid medium may also contain one or more anticoagulants, such as heparin, or one or more clotting agents, such as thrombin.

The particles may have a mean size falling in a range having a lower limit of about 20 $\mu$m and an upper limit of about 10 mm, possibly with a lower limit of about 30 $\mu$m and an upper limit of about 10 mm or a range with a lower limit of about 45 $\mu$m and an upper limit of about 2800 $\mu$m. Several tailored size ranges are applicable: 1.) lower limit of about 90 $\mu$m and an upper limit of about 2000 $\mu$m, 2.) a lower limit of about 180 $\mu$m and an upper limit of about 1400 $\mu$m, 3.) a lower limit of about 300 $\mu$m and an upper limit of about 1000 $\mu$m, 4.) a lower limit of about 500 $\mu$m and an upper limit of about 750 $\mu$m, 5.) a lower limit of about 180 $\mu$m and an upper limit of about 300 $\mu$m, 6.) a lower limit of about 300 $\mu$m and an upper limit of about 500 $\mu$m, and 7.) a lower limit of about 500 $\mu$m and an upper limit of about 710 $\mu$m.

Similarly, the particle porosity may fall in a range having a lower limit of about 50% and has an upper limit of about 98%, perhaps with a lower limit of about 80% and an upper limit of about 96%.

Combinations of these particle sizes and porosities and the liquid medium specific gravity are suitable for the composition, e.g., where the particle size has a lower limit of about 30 $\mu$m and an upper limit of about 10 mm and where the liquid medium specific gravity has a lower limit of about 1.0 and an upper limit of about 1.50; or perhaps, where the particle size falls in a range that has a lower limit of about 180 $\mu$m and an upper limit of about 710 $\mu$m and where the liquid medium specific gravity has a lower limit of about 1.2 and an upper limit of about 1.4.

Combinations suitable for certain liquid medium include those where the particle porosity has a lower limit of about 50% and has an upper limit of about 98% and where the liquid medium specific gravity has a lower limit of about 1.0 and has an upper limit of about 1.50; a particle porosity with a lower limit of about 80% an upper limit of about 96% and where the liquid medium specific gravity has a lower limit of about 1.2 and an upper limit of about 1.4.

The particles may further comprise radio-opacifiers, antibiotics, chemotherapy drugs, pharmaceuticals, growth factors, anti-growth factors, and natural and synthetic hormones as well as imaging or contrast agents such as barium sulfate, gold, tantalum, platinum, tungsten, bismuth oxide, and mixtures.

The particles may contain one or more anticoagulants such as heparin and one or more clotting agents, such as thrombin.

The particles may be diminuted to an appropriate size or size range distribution by, e.g., grinding, cutting, chopping, die cutting, etc., prior to their introduction into the liquid medium.

The resulting composition generally contains particles, when properly selected, that are generally homogeneous or evenly distributed throughout the liquid medium for a period of time at least adequate to perform a normal embolization procedure. This homogeneity of particles in the liquid medium allows the particle/liquid combination to be substantially non-clogging when passed through a catheter delivery system and permits a predictable and even delivery of the particles.

Additionally, the particles and medium may be associated, perhaps in a physical kit, for producing the dispersed or homogeneous composition.

The method for producing the partially acetalized polyvinyl alcohol foam or sponge particles is made up of the steps of mixing polyvinyl alcohol reactant, at least one acidic catalyst, and at least one acetalizing agent under reactions conditions suitable for forming partially acetalized foam particles. The reaction medium may be stirred, perhaps after the combination of at least one substantially non-reactive liquid phase, such as water or an aqueous starch or aqueous polyethylene oxide or aqueous polyethylene glycol mixture, with the polyvinyl alcohol reactant.

The polyvinyl alcohol reactant may have a viscosity average molecular weight in a range having a lower boundary of 50,000 and an upper boundary of 200,000 or in a range having a lower boundary of 125,000 and an upper boundary of 175,000. The polyvinyl alcohol reactant may have a percentage of saponification in a range having a lower boundary of 75% and an upper boundary of 99.3% or in a range having a lower boundary of 85% and an upper boundary of 95%.

The acetalization reaction is acid catalyzed by at least one organic acid, such as carboxylic acids, formic acid, acetic acid, propionic acid, butanoic acid, isobutanoic acid, pentanoic acid, caproic acid, caprylic acid, capric acid, benzoic acid and oxalic acid or by at least one inorganic acid, such as the salts of hydroacids, hydrochloric acid, hydrobromic acid and hydrofluoric acid; salts of oxoacids, sulfuric acid, nitric acid, phosphoric acid, carbonic acid, boric acid, chloric acid, silicic acid, perchloric acid, chlorous acid, hypochlorous acid, chlorosulfuric acid, amidosulfuric acid, disulfuric acid and tripolyphosphoric acid; salts of thioacids, and thiosulfuric acid.

The reactant acetalizing agent may be at least one member selected from the group consisting of formaldehyde, formaldehyde dimethyl acetal, acetaldehyde, propylaldehyde, butyraldehyde, pentaldehyde, glutaraldehyde, long chain aldehydes containing at least six C atoms, trioxane, paraformaldehyde, benzaldehyde, phenylacetaldehyde, and their mixtures.

Typically, the reaction sequence will also include the steps of stirring the mixture, aging the mixture, washing the mixture to remove additional reactants or acidic catalyst, separating the particles, and grinding the particles. Ground particles may be separated into specific size ranges by, e.g., sieving them.

Particles produced by these methods form a component of this invention.

A following and separate procedure involves selecting appropriate partially hydrolyzed polyvinyl alcohol foam particles produced by the processes discussed above appropriate for a particular injectable, biologically acceptable, liquid medium such that, once hydrolyzed, the particles are substantially suspendable or suspended in the selected liquid medium. The next step involves combining the selected particles and the medium to hydrate the particles and to produce the composition.

DESCRIPTION OF THE INVENTION

Described below are chemical processes for forming partially acetalized polyvinyl alcohol foam particles having particle size, pore size, density and particle porosity that are suitable for inclusion in selected injectable, biologically acceptable, liquid media having a liquid medium specific gravity and desirably are dispersed sufficiently so not to aggregate nor to clump in delivery equipment during an embolization procedure. The particles may be substantially homogeneously suspended in the medium to so prevent the clogging.

The methods for producing the partially acetalized polyvinyl alcohol foam or sponge particles are made up of: the steps of mixing polyvinyl alcohol reactant, at least one acidic catalyst, and at least one acetalizing agent under reaction conditions suitable for forming partially acetalized foam particles. The reaction medium may be stirred, perhaps after the combination of at least one substantially non-reactive liquid phase, such as water or an aqueous starch mixture or aqueous polyethylene oxide or aqueous polyethylene glycol mixture, with the polyvinyl alcohol reactant. Alternatively, the reaction medium may be air-whipped prior to the acetalization reaction step thereby forming an air-whipped foam.

The polyvinyl alcohol reactant may have a viscosity average molecular weight in a range having a lower boundary of 50,000 and an upper boundary of 200,000 or in a range having a lower boundary of 125,000 and an upper boundary of 175,000. The polyvinyl alcohol reactant may have a percentage of saponification in a range having a lower boundary of 75% and an upper boundary of 99.3% or in a range having a lower boundary of 85% and an upper boundary of 95%.

The acetalization reaction is acid catalyzed. The catalyst may be: a.) at least one organic acid, such as carboxylic acids, formic acid, acetic acid, propionic acid, butanoic acid, isobutanoic acid, pentanoic acid, caproic acid, caprylic acid, capric acid, benzoic acid and oxalic acid or b.) at least one inorganic acid, such as the salts of hydroacids, hydrochloric acid, hydrobromic acid and hydrofluoric acid; salts of oxoacids, sulfuric acid, nitric acid, phosphoric acid, carbonic acid, boric acid, chloric acid, silicic acid, perchloric acid, chlorous acid, hypochlorous acid, chlorosulfuric acid, amidosulfuric acid, disulfuric acid and tripolyphosphoric acid; salts of thioacids, and thiosulfuric acid. Obviously, the catalyst may be of mixtures or combinations of any of these.

The reactant acetalizing agent may be any compound performing the acetalization function, but may be at least one member selected from the group consisting of formaldehyde, formaldehyde dimethyl acetal, acetaldehyde, propylaldehyde, butyraldehyde, pentaldehyde, glutaraldehyde, long chain aldehydes (e.g., containing at least six C atoms), trioxane, paraformaldehyde, benzaldehyde, phenylacetaldehyde, and their mixtures.

Typically, the reaction sequence will also include the steps of stirring the mixture, aging the mixture at a modestly elevated temperature, e.g., about 30° C. to about 65° C. (to achieve an acceptable level of conversion to acetal), washing the mixture to remove extraneous reactants and the acidic catalyst, separating the particles, and grinding, cutting, chopping, or die cutting the particles to suitable sizes. These particles may be separated into specific size ranges by, e.g., sieving them or by other appropriate sizing or separating procedures.

As is shown in detail in the Examples below, we have observed that varying the following reaction or reactant parameters directionally from the reaction conditions found in those Examples produces the following changes to the particles. Lowering the molecular weight of the feed polyvinyl alcohol generally lowers the overall biocompatibility, elasticity, tear strength, and resilience of the resulting particle. Raising the molecular weight of the feed polyvinyl alcohol has the opposite effect on those particle parameters.

For the practical reaction parameters discussed here, lowering the degree of hydrolysis of the feed polyvinyl alcohol generally increases both the level of achievable hydration and the rate at which the particle may be hydrated or hydrates. Such a change increases the elasticity and resilience of the product particle. Raising the degree of hydrolysis (or degree of saponification) of the feed polyvinyl alcohol causes the opposite effects to occur.

Similarly, within the scope of practical reaction conditions suitable for the particles discussed here, the extent of the reaction or conversion to acetal may be used to control the following particle parameters: Lowering the extent of the reaction or conversion to acetal again increases both the level of achievable hydration and the rate at which the particle may be hydrated or hydrates, elasticity, resilience, and compressibility of the product particle but lowers the resulting modulus. Again raising the extent of reaction will have the opposite effects on the product particle.

We have observed that an increase of the initial reaction rate, e.g., perhaps by increase of the initial reaction temperature or by increase in the catalyst or acetalizing agent concentration or any or all of these changes, lowers the particles' cell or pore size. Lowering that initial rate increases the size of those pores or cells.

The directional changes outlined above are used to tailor a particle suitable for suspension in a selected liquid delivery medium.

The overall effects of the product particle parameters in an embolization procedure are these: as the bulk and polymer modulus or the polymer density go down, the particles become generally more compressible, conform to the tissue site more easily, and are able to penetrate further and pack more efficiently at the treatment site. Numerically higher values of these parameters also cause higher point forces on delicate vessel surfaces. Likewise, if the polymer and bulk modulus and density are higher and compressibility becomes lower, the penetration to a vessel treatment site is compromised or limited due to aggregation of inflexible particles.

Pore size has the following effect on particle uniformity. Larger pores, in comparison to the size of the particle, may yield a particle having extraneous material hanging on the edges. These projections likely accentuate clogging in the delivery device via mechanical interlocking. Conversely, particles with pores smaller by comparison with the particle diameter generally have more of a spherical shape and are less likely to clog during delivery. Packing in a vascular cavity is typically more efficient, as well. Other practical effects of particle pore (or cell) size as deposited in the vasculature are that small pores (generally <200 um) do not permit ease of tissue in-growth. Larger cell sizes permit a high degree of tissue in-growth.

Porosity of the product foam particle (a value inversely related to the bulk foam, or relative, density) exhibits the following in this polymer system: lowering the porosity increases the bulk foam density, bulk modulus, and resilience but lowers the particle's compressibility. Raising the porosity has opposite effects.

In the reactive phase-separation process (all of the examples used in this application), the bulk density and porosity are controlled primarily through the relative proportion of intial PVAOH in the system. A greater amount of non-reactive phase (lower relative PVAOH) will ultimately wash out leaving a lower bulk density and higher porosity. Care must be taken to include an appropriate starting amount of PVAOH, since too low an initial initial PVAOH amount will result in a collapsed solid mass.

In the air-whipped process the bulk density is controlled by the amount of air whipped into the polymer. The greater the proportion of air, the greater the porosity and lower bulk density.

The resultant degree of hydration inherent in the produced particle has several effects: if a particle exhibits lower hydration, it is generally less biocompatible and is generally less able to imbibe hydrophilic agents or solutions. The ability to imbibe non-hydrophilic agents is to be observed on a case-to-case basis.

A high particle hydration rate, that is, during the period just prior to introduction into the body, is desirable because the particle is more rapidly suspended in the carrier medium. Particles having comparatively lower hydration rates may initially float or sink depending upon bulk foam density and morphology and slow the period of time required for the embolization procedure.

In any case, the particles produced by these methods and described here form a component of this invention.

A following and separate procedure involves selecting appropriate partially acetalized polyvinyl alcohol foam particles produced by the processes discussed above appropriate for a particular injectable, biologically acceptable, liquid medium such that, once hydrolyzed, the particles are substantially suspendable or suspended in the selected liquid medium. The next step involves combining the selected particles and the medium to hydrate the particles and to produce the composition.

The embolic composition used for forming an occlusion in a body opening or cavity, is a combination of hydrated, partially acetalized, polyvinyl alcohol foam particles made in the fashion described above and have particle size, pore sizes, and particle porosities selected to be generally suspended in a matched, selected injectable, biologically acceptable, liquid media. The homogeneous suspension generally provides for a predictable and even delivery of the particles to the selected site without clogging the delivery apparatus.

The liquid media has a liquid medium specific gravity, generally in a range having a lower limit of about 1.0 and has an upper limit of about 1.50, although the liquid medium specific gravity may fall in a range with a lower limit of about 1.1 and an upper limit of about 1.40, or a lower limit of about 1.15 and an upper limit of about 1.40.

The liquid medium may be made up of one or more members selected from the group consisting of saline solution, radio-opacifiers, antibiotics, chemotherapy drugs, pharmaceuticals, growth factors, anti-growth factors, and natural and synthetic hormones or, perhaps one or more imaging or contrast agents. The radio-opacifiers may comprise one or more iodine-based imaging or contrast agents such as the well known and commercially available Oxilan 300, Oxilan 350, Ultravist 150, Ultravist 240, Ultravist 300, Ultravist 370, and Omnipaque 350.

For certain uses, the liquid medium may also contain one or more anticoagulants, such as heparin., or one or more clotting agents, such as thrombin.

The particles may have a mean size falling in a range having a lower limit of about 20 $\mu$m and an upper limit of about 10 mm, possibly with a lower limit of about 30 $\mu$m and an upper limit of about 10 mm or a range with a lower limit of about 45 $\mu$m and an upper limit of about 2800 $\mu$m. Several tailored size ranges are applicable: 1.) lower limit of about 90 $\mu$m and an upper limit of about 2000 $\mu$m, 2.) a lower limit of about 180 $\mu$m and an upper limit of about 1400 $\mu$m, 3.) a lower limit of about 300 $\mu$m and an upper limit of about 1000 $\mu$m, 4.) a lower limit of about 500 $\mu$m and an upper limit of about 750 $\mu$m, 5.) a lower limit of about 180 $\mu$m and an upper limit of about 300 $\mu$m, 6.) a lower limit of about 300 $\mu$m and an upper limit of about 500 $\mu$m, and 7.) a lower limit of about 500 $\mu$m and an upper limit of about 710 $\mu$m.

Similarly, the particle porosity may fall in a range having a lower limit of about 50% and has an upper limit of about 98%, perhaps with a lower limit of about 80% and an upper limit of about 96%.

Combinations of these particle sizes and porosities and the liquid medium specific gravity are suitable for the composition, e.g., where the particle size has a lower limit of about 30 μm and an upper limit of about 10 mm and where the liquid medium specific gravity has a lower limit of about 1.0 and an upper limit of about 1.50; or perhaps, where the particle size falls in a range that has a lower limit of about 180 μm and an upper limit of about 710 μm and where the liquid medium specific gravity has a lower limit of about 1.2 and an upper limit of about 1.4.

Combinations suitable for certain liquid medium include those where the particle porosity has a lower limit of about 50% and has an upper limit of about 98% and where the liquid medium specific gravity has a lower limit of about 1.0 and has an upper limit of about 1.50; a particle porosity with a lower limit of about 80% an upper limit of about 96% and where the liquid medium specific gravity has a lower limit of about 1.2 and an upper limit of about 1.4.

The particles may further comprise radio-opacifiers, antibiotics, chemotherapy drugs, pharmaceuticals, growth factors, anti-growth factors, and natural and synthetic hormones as well as imaging or contrast agents such as barium sulfate, gold, tantalum, platinum, tungsten, bismuth oxide, and mixtures.

The particles themselves may contain one or more anticoagulants such as heparin and one or more clotting agents, such as thrombin in certain rarely chosen instances.

The particles may be sized, e.g., ground, cut, chopped, or die-cut, to suitable sizes prior to their introduction into the liquid medium.

The resulting composition generally is substantially non-clogging when passed through a catheter delivery system; the homogeneous suspension also generally provides for a predictable and even delivery of the particles.

Additionally, the particles and medium may be associated, perhaps in a physical kit, for producing the dispersed composition by the hydration procedure discussed above.

EXAMPLES

Example 1

A mixture of 100 of polyvinyl alcohol (PVAOH), having a viscosity average molecular weight range of 85,000 to 146,000 and a percentage of saponification of approximately 99% and 736 g of deionized water was heated to 95° C. for thirty minutes and set aside and allowed to cool to room temperature. A separate mixture of 20 g of potato starch 180 g of deionized water was heated to 80° C. and then added to the PVAOH solution and mixed thoroughly. To this resultant solution was added 45 g of approximately 98% sulfuric acid and 76 g of approximately 37% formaldehyde (formalin solution) to form the reactant mixture. After thorough stirring the reactant mixture was cured at 35° C. for 6 hours and then 55° C. for 6 hours and allowed to cool to room temperature.

The resultant partially acetalized polyvinyl alcohol (PVAt) sponge was then washed thoroughly to remove excess formaldehyde and sulfuric acid. The sponge was then ground into particles in a blender operating at approximately 20,000 RPM for 10 minutes with added water in ratio to sponge of approximately 2:1. The resultant particles were isolated through a #325 mesh screen and dried at 50° C. overnight. The particles were then separated into size ranges using ASTM standard sieves according to the table below.

| ASTM Sieve # | Sieve opening (μm) | Particle Size Lower (μm) | Particle Size Upper (μm) |
|---|---|---|---|
| 7 | 2,800 | 2,800 | N/A |
| 10 | 2,000 | 2,000 | 2,800 |
| 14 | 1,400 | 1,400 | 2,000 |
| 18 | 1,000 | 1,000 | 1,400 |
| 25 | 710 | 710 | 1,000 |
| 35 | 500 | 500 | 710 |
| 50 | 300 | 300 | 500 |
| 80 | 180 | 180 | 300 |
| 170 | 90 | 90 | 180 |
| 325 | 45 | 45 | 90 |

The particles hydrated slowly with consequent floating in solution early in the hydration process. We believe this to be due to the relatively high hydrolysis of the base or feed polymer and the consequent relatively high resistance to water absorption. Such a result would translate into a relatively slower hydration rate. Furthermore, the higher degree of hydrolysis allows for a more ordered association between polymer chains giving a high surface energy and thereby variously inhibiting the wetting (e.g., air bubbles were surface trapped) and slowing the hydration rate.

Example 2

We repeated the same procedure as that of Example 1 except that the percentage of saponification of the PVAOH was approximately 88%.

We noted a more rapid hydration of particles with a subsequent suspension in solution early in the hydration process.

We believe that although the reaction composition and conditions were substantially identical to those in Example 1, the lower degree of hydrolysis of the base polymer permitted the rapid and more extensive water absorption. This is believed to be due to the less-ordered nature of the polymer chains—residual acetate groups disrupting chain alignment. The extensive water absorption allows for a closer approximation of the particle to the density of the solution (water).

Example 3

The same procedure as that of example 2 was repeated except that the temperature profile of the curing step was 55° C. for 16 hours.

These particles exhibited rapid hydration followed by their 'separation' from water by sinking. We believe that, although the reaction composition is identical to Example 2), the extended period of reaction at the elevated temperature caused a greater extent of conversion to the acetal functionality. The acetate residuals inherent in the base polymer permitted for surface hydration, but the extensive degree of conversion and crosslinking resulted in a tight network unable to imbibe water to the same degree. The density of the resultant polymer was greater than the water, thus it sank.

Example 4

The procedure of Example 2 was repeated except that the mass of formalin solution was 85 g. These particles rapidly hydrated of particles and sank in the water.

Although the reaction temperature profile was identical to that of Example 2), the greater concentration of formaldehyde caused a greater extent of conversion to the acetal functionality. The result was nevertheless the same as seen in Example 3). In this instance, though, we believe that the result was due to the concentration variance instead of the temperature. The rate and extent of the acetal formation reaction is known to be directly related to temperature and HCHO concentration (Arrhenius kinetics and 2nd order with [PVAOH:HCHO]).

We claim as our invention:

1. A composition for forming an occlusion in a body opening or cavity comprising hydrated, partially acetalized, polyvinyl alcohol foam particles having particle size, pore size, and particle porosity, the particles being substantially suspended in a selected injectable, biologically acceptable, liquid medium having a liquid medium specific gravity.

2. The composition of claim 1 where the liquid medium specific gravity has a has a lower limit of about 1.0 and has an upper limit of about 1.50.

3. The composition of claim 1 where the liquid medium specific gravity has a has a lower limit of about 1.1 and has an upper limit of about 1.40.

4. The composition of clam 1 where the liquid medium specific gravity has a has a lower limit of about 1.15 and has an upper limit of about 1.40.

5. The composition of claim 1 where the liquid medium comprises one or more members selected from the group consisting of saline solution, radio-opacifiers, MR contrast agents, negative contrast agents, antibiotics, chemotherapy drugs, pharmaceuticals, growth factors, anti-growth factors, and natural and synthetic hormones.

6. The composition of claim 5 where the liquid medium comprises one or more MR contrast agents.

7. The composition of claim 5 where the liquid medium comprises one or more gaseous negative contrast agents.

8. The composition of claim 6 where the liquid medium comprises one or more MR contrast agents selected from hyperpolarized xenon, argon, and helium.

9. The composition of claim 7 where the liquid medium comprises $CO_2$.

10. The composition of claim 5 where the radio-opacifiers comprise one or more imaging or contrast agents.

11. The composition of claim 5 where the radio-opacifiers comprise one or more iodine-based imaging or contrast agents.

12. The composition of claim 5 where the radio-opacifiers comprise one or more members selected from the group consisting of Oxilan 300, Oxilan 350, Ultravist 150, Ultravist 240, Ultravist 300, Ultravist 370, and Omnipaque 350.

13. The composition of claim 5 where the radio-opacifiers comprise one or more solid imaging or contrast agents.

14. The composition of claim 5 where the radio-opacifiers comprise one or more members selected from the group consisting of barium sulfate, gold, tantalum, platinum, tungsten, bismuth oxide, and mixtures.

15. The composition of claim 1 where the liquid medium further comprises one or more anticoagulants.

16. The composition of claim 15 where the one or more anticoagulants comprises heparin.

17. The composition of claim 1 where the liquid medium further comprises one or more clotting agents.

18. The composition of claim 1 where the liquid medium further comprises thrombin.

19. The composition of claim 1 where the particle size has a lower limit of about 20 $\mu$m and has an upper limit of about 10 mm.

20. The composition of claim 1 where the particle size has a lower limit of about 30 $\mu$m and has an upper limit of about 10 mm.

21. The composition of claim 1 where the particle size has a lower limit of about 45 $\mu$m and has an upper limit of about 2800 $\mu$m.

22. The composition of claim 1 where the particle size has a lower limit of about 90 $\mu$m and has an upper limit of about 2000 $\mu$m.

23. The composition of claim 1 where the particle size has a lower limit of about 180 $\mu$m and has an upper limit of about 1400 $\mu$m.

24. The composition of claim 1 where the particle size has a lower limit of about 300 $\mu$m and has an upper limit of about 1000 $\mu$m.

25. The composition of claim 1 where the particle size has a lower limit of about 500 $\mu$m and has an upper limit of about 750 $\mu$m.

26. The composition of claim 1 where the particle size has a lower limit of about 180 $\mu$m and has an upper limit of about 300 $\mu$m.

27. The composition of claim 1 where the particle size has a lower limit of about 300 $\mu$m and has an upper limit of about 500 $\mu$m.

28. The composition of claim 1 where the particle size has a lower limit of about 500 $\mu$m and has an upper limit of about 720 $\mu$m.

29. The composition of claim 1 where the particle porosity has a lower limit of about 50% and has an upper limit of about 98%.

30. The composition of claim 29 where the particle porosity has a lower limit of about 80% and has an upper limit of about 96%.

31. The composition of claim 1 where the particle size has a lower limit of about the particle size has a lower limit of about 30 $\mu$m and has an upper limit of about 10mm and where the liquid medium specific gravity has a has a lower limit of about 1.0 and has an upper limit of about 1.50.

32. The composition of claim 31 where the particle size has a lower limit of about the particle size has a lower limit of about 180 $\mu$m and has an upper limit of about 710 $\mu$m and where the liquid medium specific gravity has a has a lower limit of about 1.2 and has an upper limit of about 1.4.

33. The composition of claim 1 where the particle porosity has a lower limit of about 50% and has an upper limit of about 98% and where the liquid medium specific gravity has a has a lower limit of about 1.0 and has an upper limit of about 1.50.

34. The composition of claim 33 where the particle porosity has a lower limit of about 80% and has an upper limit of about 96% and where the liquid medium specific gravity has a has a lower limit of about 1.2 and has an upper limit of about 1.4.

35. The composition of claim 1 where the particles further comprise one or more members selected from the group consisting of radio-opacifiers, antibiotics, chemotherapy drugs, pharmaceuticals, growth factors, anti-growth factors, and natural and synthetic hormones.

36. The composition of claim 35 where the radio-opacifiers comprise one or more imaging or contrast agents.

37. The composition of claim 35 where the radio-opacifiers comprise one or more solid imaging or contrast agents.

38. The composition of claim 35 where the radio-opacifiers comprise one or more members selected from the group consisting of barium sulfate, gold, tantalum, platinum, tungsten, bismuth oxide, and their mixtures.

39. The composition of claim 35 where the particles further comprise one or more anticoagulants.

40. The composition of claim 39 where the anticoagulant comprises heparin.

41. The composition of claim 35 where the particles further comprise one or more clotting agents.

42. The composition of claim 41 where the particles further comprise thrombin.

43. The composition of claim 1 wherein the particles have been reduced in size prior to introduction into the liquid medium.

44. The composition of claim 1 that is substantially homogeneous when passed through a catheter delivery system.

45. The composition of claim 1 that is substantially non-clogging when passed through a catheter delivery system.

46. A kit for producing a composition of hydrated, substantially suspended, partially acetalized polyvinyl alcohol foam particles having particle size, pore size, and particle porosity and an injectable, biologically acceptable, liquid medium, comprising in combination, physically unmixed:
a.) non-hydrated, partially acetalized polyvinyl alcohol foam particles having particle parameters selected so that, when hydrated, said particles become substantially suspended in the liquid medium, and b.) the injectable, biologically acceptable, liquid medium.

47. The kit of claim 46 where the liquid medium specific gravity has a has a lower limit of about 1.0 and has an upper limit of about 1.50.

48. The kit of claim 46 where the liquid medium comprises one or more members selected from the group consisting of saline solution, radio-opacifiers, MR contrast agents, negative contrast agents, antibiotics, chemotherapy drugs, pharmaceuticals, growth factors, anti-growth factors, and natural and synthetic hormones.

49. The kit of claim 48 where the liquid medium comprises one or more MR contrast agents.

50. The kit of claim 48 where the liquid medium comprises one or more gaseous negative contrast agents.

51. The kit of claim 49 where the liquid medium comprises one or more gaseous MR contrast agents selected from hyperpolarized xenon, argon, and helium.

52. The kit of claim 50 where the liquid medium comprises $CO_2$.

53. The kit of claim 46 where the radio-opacifiers comprise one or more imaging or contrast agents.

54. The kit of claim 46 where the radio-opacifiers comprise one or more iodine-based imaging or contrast agents.

55. The kit of claim 46 where the liquid medium further comprises one or more anticoagulants.

56. The kit of claim 55 where the anticoagulant comprises heparin.

57. The kit of claim 50 where the liquid medium further comprises one or more clotting agents.

58. The kit of claim 50 where the liquid medium further comprises thrombin.

59. The kit of claim 50 where the particle size has a lower limit of about 20 μm and has an upper limit of about 10 mm.

60. The kit of claim 50 where the particle porosity has a lower limit of about 50% and has an upper limit of about 97%.

61. The kit of claim 50 where the particle size has a lower limit of about 30 μm and has an upper limit of about 10mm and where the liquid medium specific gravity has a has a lower limit of about 1.0 and has an upper limit of about 1.50.

62. The kit of claim 50 where the particle porosity has a lower limit of about 50% and has an upper limit of about 97% and where the liquid medium specific gravity has a has a lower limit of about 1.0 and has an upper limit of about 1.50.

63. The kit of claim 50 where the particles further comprise one or more members selected from the group consisting of radio-opacifiers, antibiotics, chemotherapy drugs, pharmaceuticals, growth factors, anti-growth factors, and natural and synthetic hormones.

64. The kit of claim 63 where the radio-opacifiers comprise one or more imaging or contrast agents.

65. The kit of claim 63 where the radio-opacifiers comprise one or more solid imaging or contrast agents.

66. The kit of claim 63 where the radio-opacifiers comprise one or more members selected from the group consisting of barium sulfate, gold, tantalum, platinum, tungsten, bismuth oxide, and mixtures.

67. The kit of claim 50 where the particles further comprise one or more anticoagulants.

68. The kit of claim 50 where the anticoagulant comprises heparin.

69. The kit of claim 50 where the particles further comprise one or more clotting agents.

70. The kit of claim 50 where the particles further comprise thrombin.

71. A method for producing partially acetalized polyvinyl alcohol foam particles having a substantially homogeneous particle size and having a particle porosity, the particles being substantially suspendable in a selected injectable, biologically acceptable, liquid medium having a liquid medium specific gravity, comprising the steps of mixing polyvinyl alcohol reactant, at least one acidic catalyst, and at least one acetalizing agent under reactions conditions suitable for forming partially acetalized foam particles.

72. The method of claim 71 wherein the polyvinyl alcohol reactant has a viscosity average molecular weight in a range having a lower boundary of 50,000 and an upper boundary of 200,000.

73. The method of claim 71 wherein the polyvinyl alcohol reactant has a viscosity average molecular weight in a range having a lower boundary of 75,000 and an upper boundary of 175,000.

74. The method of claim 71 wherein the polyvinyl alcohol reactant has a percentage of saponification in a range having a lower boundary of 75% and an upper boundary of 99.5%.

75. The method of claim 71 wherein the polyvinyl alcohol reactant has a viscosity average molecular weight in a range having a lower boundary of 50,000 and an upper boundary of 200,000.

76. The method of claim 71 wherein the substantially non-reactive liquid phase is aqueous.

77. The method of claim 71 wherein the substantially non-reactive liquid phase comprises water.

78. The method of claim 71 wherein the substantially non-reactive liquid phase comprises an aqueous thickener.

79. The method of claim 71 wherein the substantially non-reactive liquid phase comprises an aqueous starch suspension.

80. The method of claim 71 wherein the acidic catalyst comprises at least one organic acid.

81. The method of claim 80 wherein the at least one organic acid catalyst comprises a member selected from the group consisting of carboxylic acids, formic acid, acetic acid, propionic acid, butanoic acid, isobutanoic acid, pentanoic acid, caproic acid, caprylic acid, capric acid, benzoic acid and oxalic acid.

82. The method of claim 71 wherein the acidic catalyst comprises at least one inorganic acid.

83. The method of claim 82 wherein the at least one organic acid catalyst comprises a member selected from the group consisting of salts of hydroacids, hydrochloric acid, hydrobromic acid and hydrofluoric acid; salts of oxoacids, sulfuric acid, nitric acid, phosphoric acid, carbonic acid, boric acid, chloric acid, silicic acid, perchloric acid, chlorous acid, hypochlorous acid, chlorosulfuric acid, amidosulfuric acid, disulfuric acid and tripolyphosphoric acid; salts of thioacids, and thiosulfuric acid.

84. The method of claim 71 wherein the at least one acetalizing agent is at least one member selected from the group consisting of formaldehyde, formaldehyde dimethyl acetal, acetaldehyde, propylaldehyde, butyraldehyde, pentaldehyde, glutaraldehyde, long chain aldehydes containing at least six C atoms, trioxane, paraformaldehyde, benzaldehyde, phenylacetaldehyde, and mixtures.

85. The method of claim 71 further comprising the combination of at least one substantially non-reactive liquid phase with the polyvinyl alcohol reactant.

86. The method of claim 85 further comprising the step of stirring the mixture.

87. The method of claim 86 further comprising the step of washing the mixture.

88. The method of claim 87 further comprising the step of separating particles.

89. The method of claim 88 further comprising the step of dimuniting the particles.

90. The method of claim 85 further comprising the step of separating the particles into size ranges.

91. Particles produced by the method of claim 1.

92. Particles produced by the method of claim 88.

93. Particles produced by the method of claim 89.

94. Particles produced by the method of claim 90.

95. The method of claim 71 further comprising the step of air-whipping the mixture.

96. The method of claim 95 further comprising the step of washing the mixture.

97. The method of claim 96 further comprising the step of separating particles.

98. The method of claim 97 further comprising the step of dimuniting the particles.

99. The method of claim 98 further comprising the step of separating the particles into size ranges.

100. Particles produced by the method of claim 96.

101. Particles produced by the method of claim 97.

102. Particles produced by the method of claim 98.

103. Particles produced by the method of claim 99.

104. A method for producing a composition comprising hydrated, partially hydrolyzed polyvinyl alcohol foam particles substantially suspended in an injectable, biologically acceptable, liquid medium, comprising the steps of:

a.) selecting the injectable, biologically acceptable, liquid medium, the liquid medium having a liquid medium specific gravity, b.) selecting partially hydrolyzed polyvinyl alcohol foam particles produced by the process of any of claims 71–90 or 95–99 that, once hydrolyzed, are substantially suspendable in said selected liquid medium, and c.) combining the selected particles from step b.) and the medium of step a.) to hydrate said particles and to produce the composition.

105. The method of claim 104 further comprising the steps of producing said particles using the methods of any of claims 71–90 or 95–99.

106. The method of claim 104 where the liquid medium specific gravity has a has a lower limit of about 1.0 and has an upper limit of about 1.50.

107. The method of claim 104 where the liquid medium specific gravity has a has a lower limit of about 1.1 and has an upper limit of about 1.40.

108. The method of claim 104 where the liquid medium specific gravity has a has a lower limit of about 1.15 and has an upper limit of about 1.40.

109. The method of claim 104 where the liquid medium comprises one or more members selected from the group consisting of saline solution, radio-opacifiers, antibiotics, chemotherapy drugs, pharmaceuticals, growth factors, anti-growth factors, and natural and synthetic hormones.

110. The method of claim 109 where the liquid medium contains at least one radio-opacifier comprising one or more imaging or contrast agents.

111. The method of claim 109 where the liquid medium contains at least one radio-opacifier comprising one or more iodine-based imaging or contrast agents.

112. The method of claim 111 where the at least one radio-opacifier comprises one or more members selected from the group consisting of Oxilan 300, Oxilan 350, Ultravist 150, Ultravist 240, Ultravist 300, Ultravist 370, and Omnipaque 350.

* * * * *